United States Patent [19]
Davis et al.

[11] Patent Number: 5,397,699
[45] Date of Patent: Mar. 14, 1995

[54] METHOD FOR STABILIZING AN ALKANOL AMINE BUFFER USED IN OPTICAL DETERMINATIONS OF ENZYME ACTIVITY

[75] Inventors: James E. Davis, Wilmington; Hon-Peng P. Lau, Hockessin; Neel V. Neelkantan, Newark, all of Del.

[73] Assignee: E.I. Du Pont de Nemours and Company, Wilmington, Del.

[21] Appl. No.: 206,242

[22] Filed: Mar. 4, 1994

Related U.S. Application Data

[63] Continuation of Ser. No. 937,813, Aug. 31, 1992, abandoned.

[51] Int. Cl.$^6$ ............................................. G01N 33/553
[52] U.S. Cl. ........................................ 435/7.94; 435/6; 435/7.92; 435/7.93; 435/962; 564/2
[58] Field of Search ................... 435/7.94, 962, 7.93, 435/6, 7.92; 564/2

[56] References Cited

U.S. PATENT DOCUMENTS

| | | | |
|---|---|---|---|
| 3,207,790 | 9/1965 | Glew et al. | 260/584 |
| 3,535,260 | 10/1970 | Singh | 252/189 |
| 3,567,779 | 3/1971 | Currier et al. | 260/584 |
| 3,742,059 | 6/1973 | Dowd | 260/584 R |
| 4,824,784 | 4/1989 | Cantarow | 435/7.94 |
| 4,840,777 | 6/1989 | Faucher | 423/229 |
| 4,885,240 | 12/1989 | Wu | 435/34 |
| 4,892,817 | 1/1990 | Pawlak | 435/21 |
| 5,113,017 | 5/1992 | Smith et al. | 564/2 |
| 5,135,847 | 8/1992 | Hoke | 435/7.94 |

FOREIGN PATENT DOCUMENTS

| | | | |
|---|---|---|---|
| 0042969 | 1/1982 | European Pat. Off. | C12N 9/96 |
| 0054096 | 6/1982 | European Pat. Off. | C12Q 1/58 |
| 0166505 | 1/1986 | European Pat. Off. | C12Q 1/42 |
| 0238302 | 9/1987 | European Pat. Off. | A61K 7/42 |
| 0369362A3 | 5/1990 | European Pat. Off. | C12Q 1/42 |

OTHER PUBLICATIONS

"Reagent for Analysis of Alkali Phosphatase," Database, WPI Week 7613, Derwent Publications Ltd., AN 76-23250X & JP51016989, Wako Pure Chem Ind KK, Feb. 10, 1976.

Rej, R. and Bretaudiere, J-P, "Effects of Metal Ions on the Measurement of Alkaline Phosphatase Activity," Clinical Chemistry, vol. 26, No. 3, Mar. 1980, pp. 423–428.

Thompson, R. Q. et al., "Zeptomole detection limit for alkaline phosphatase using 4-aminophenylphosphate, amperometric detection, and an optical buffer system," Analytica Chimica Acta, vol. 271, No. 2, Jan. 18, 1993, pp. 223–229.

Krebs, H. A., The Use of '$CO_2$ Buffers' in Manometric Measurements of Cell Metabolism, *J. Biochem*, 48, 349–359, 1951.

*Primary Examiner*—Mary E. Ceperley

[57] ABSTRACT

A method for stabilizing an alkanol amine buffer against substantial degradation so that enzyme activity can be optically determined in such a buffer is described. Stabilization is achieved by adding a stabilizing effective amount of a stabilizing agent to the buffer wherein the stabilizing agent (i) does not inhibit enzyme activity and (ii) does not interfere substantially with the optical determination in the wavelength region of measurement.

6 Claims, No Drawings

METHOD FOR STABILIZING AN ALKANOL AMINE BUFFER USED IN OPTICAL DETERMINATIONS OF ENZYME ACTIVITY

This is a continuation of application Ser. No. 07/937,813, filed Aug. 31, 1992, now abandoned.

FIELD OF THE INVENTION

This invention relates to optically determining enzymatic activity and, more particularly, to a method for stabilizing an alkanol amine buffer used in making optical determinations of enzyme activity as well as to use of such stabilized buffers in assays for detecting and/or quantitating the presence or absence of analyte.

BACKGROUND OF THE INVENTION

Enzyme assays, such as enzyme immunoassays (EIA), use enzymes as markers to quantitatively follow antigen-antibody reactions. These assays have been described in a multitude of publications like Enzyme Immunoassay, Ed., Ishikawa et al., Igaku-Shoin Ltd., Tokyo (1981).

Reagents required such as enzyme-labeled antigens and antibodies or enzyme-labeled nucleic acids are usually stable in a conventional refrigerator for years. No expensive equipment is required. These assays can be performed without much experience in the laboratory and pose no problem with respect to disposing hazardous radioactive waste materials. Indeed, enzyme assays are convenient and powerful analytical tools in a variety of research fields and clinical diagnostics.

When an enzyme is used as a label, it should be easily recognizable, stable and have catalytic activity which produces a detectable change in the substrate for that enzyme. In other words, the enzyme should maintain sufficient activity and, at the same time, should function satisfactorily under the conditions in which an assay is performed. In addition, the label must not disintegrate or deteriorate.

To be used as a label, the number of enzyme molecules must be measured quantitatively. An enzyme labeled binding assay method is based on counting the number of enzymes which are linked to antigen, antibody, or nucleic acid molecules instead of counting the latter molecules directly. However, the number of label enzyme molecules themselves cannot be counted, rather, the enzyme activity of the label is counted and the number of labels that have catalyzed the reaction can be determined. Therefore, an enzyme assay depends upon the assumption that the catalytic activity that is obtained from the physical measurement is proportional to the amount of enzyme that catalyzes this reaction.

Such measurements of enzyme activity can be affected by the pH of a solution. Thus, virtually all quantitative assays performed in aqueous solution are carried out in the presence of a buffer to control pH. A buffer is a substance which, when added to a solution, resists a change in hydrogen ion concentration on addition of acid or alkali. Selection of an appropriate buffer depends on a variety of factors such as the pH range over which it is effective, solubility, purity, stability, etc.

Since quantitative measurements often involve optical determinations by measuring changes in absorbance or emission, useful buffers should not interfere substantially with the optical determination in the Wavelength region of measurement.

Alkanol amine buffers such as triethanolamine (TEA) or diethanolamine (DEA) are used quite commonly in clinical analyses because they have useful buffer ranges, are substantially optically transparent, and generally do not prove harmful to physiological substances like enzymes, antigens, antibodies or nucleic acids.

However, such buffers have a limited shelf life. Over time, these alkanol amine buffers can form degradation products which substantially interfere with optical determinations in the wavelength region of measurement.

SUMMARY OF THE INVENTION

This invention concerns a method for stabilizing an alkanol amine buffer used in optically determining enzymatic activity which comprises adding a stabilizing effective amount of a stabilizing agent to the buffer wherein the stabilizing agent (i) does not inhibit enzyme activity and (ii) does not interfere substantially with the optical determination in the wavelength region of measurement.

In another embodiment, this invention concerns an assay for detecting and/or quantitating the presence or absence of an analyte in a sample which comprises:
  a) contacting, simultaneously or sequentially, the sample suspected to contain the analyte with a capture reagent and an enzyme-labeled detector; and
  b) optically detecting or quantitating the product of step (a) in the presence of an alkanol amine buffer, wherein the buffer has been stabilized by adding a stabilizing effective amount of a stabilizing agent to the buffer further wherein the stabilizing agent (i) does not inhibit enzyme activity and (ii) does not interfere substantially with the optical determination in a wavelength region of measurement.

DETAILED DESCRIPTION OF THE INVENTION

The term "optically determining or optical determination" as used herein means determining the quantity of light of any particular wavelength range absorbed or emitted by a solution whether by absorbance, fluorescence, phosphorescence, electroluminescence, chemiluminescence, or any other means by which such determinations can be made.

The term "wavelength region of measurement" is used interchangeably with "wavelength range".

The term "stabilizing agent" as used herein means any reagent or combination of reagents useful for stabilizing an alkanol amine buffer against substantial degradation, i.e., against degradation which substantially interferes with optically determining enzyme activity in the wavelength region of measurement. Thus, enzyme activity can be optically determined in the presence of such a "stabilized" buffer and enzyme activity is not inhibited or otherwise adversely affected by the stabilizing agent.

Specifically, the activity of any enzyme which can be used as a label or reporter can be determined in the presence of an alkanol amine buffer which has been stabilized using the method of the invention. There can be mentioned hydrolases, lyases, oxidoreductases, transferases, isomerases, and ligases. Some preferred examples include phosphatases, esterases, glycosidases and peroxidases. Specific examples include alkaline phosphatase, beta-galactosidase, and horseradish peroxidase.

Thus, the enzyme should retain sufficient activity and function under the conditions in which the optical determination is made.

As was discussed above, alkanol amine buffers are used in a wide variety of clinical analyses because they have useful buffer ranges, are substantially optically transparent and, generally, are not toxic to physiological substances such as enzymes. Examples of such buffers include mono-, di-, or triethanolamine, 2-amino-2-methyl-1,1-propanol (AMP), tris(hydroxymethyl)amino-methane (TRIS), etc.

Notwithstanding the foregoing advantages, such buffers can form degradation products during storage. This limited shelf life interferes with optical determinations in the wavelength region of measurement due to the presence of degradation products. This has a deleterious impact on obtaining accurate quantitative results.

It has been found that by stabilizing an alkanol amine buffer, such as DEA, using the method of this invention, degradation of the buffer is minimized such that enzyme activity can be optically determined in the presence of the stabilized alkanol amine buffer. Stabilization of the alkanol amine buffer is effected by adding a stabilizing effective amount of a stabilizing agent to the buffer wherein the stabilizing agent (i) does not inhibit enzyme activity and (ii) does not interfere substantially with the optical determination in the wavelength region of measurement. In other words any such interference is maintained at a level wherein accurate optical determinations of enzyme activity in an alkanol amine buffer can be made.

Stabilizing agents suitable for use in practicing the invention (i) should not inhibit enzyme activity and (ii) should not interfere substantially with the optical determination in the wavelength region of measurement. Examples of such agents include, but are not limited to, hydroxylamine, hydroxylamine hydrochloride, hydroxylamine sulfate, and other salts thereof as well as methoxylamine and other alkanolamine salts, sodium bisulfite, sodium sulfite, other metal sulfites, aluminum, zinc and other metals, etc.

A stabilizing effective amount of a stabilizing agent is an amount sufficient to minimize degradation of an alkanol amine buffer in which enzyme activity will be optically determined. For example, a stabilizing effective amount can be in the range from 0.001M to 1.0M and, more preferably, in the range from 0.015M to 0.15M.

It has been found that alkanol amine buffers can be stabilized for at least three months at room temperature and for at least one year at 4° C. using the method of the invention.

The wavelength region of measurement can be any wavelength in the electromagnetic spectrum used to optically determine enzymatic activity. Such ranges can include, for example, the visible, ultraviolet (UV), and infrared ranges.

A preferred wavelength region of measurement is in the range from 300 to 450 nm. In the case of fluorescence the preferred wavelength is about 365 nm for excitation and about 450 nm for emission.

Alkanol amine buffers stabilized in accordance with the method of the invention can be used in an assay for detecting the presence or absence of an analyte which comprises a) contacting, simultaneously or sequentially, the sample suspected to contain the analyte with a capture reagent and an enzyme-labeled detector; and b) optically detecting or quantitating the product of step (a) in the presence of an alkanol amine buffer, wherein the buffer has been stabilized by adding a stabilizing effective amount of a stabilizing agent to the buffer and further wherein the stabilizing agent (i) does not inhibit enzyme activity and (ii) does not interfere substantially with the optical determination in a wavelength region of measurement.

Examples of such assays include immunoassays and nucleic acid hybridization assays. Any format known to those skilled in the art can be used. There can be mentioned forward sandwich assays, reverse sandwich assays, competitive assays, etc. These assays can be run in solution or on a solid phase.

The capture reagent can be any reagent useful in such assays whether immunoassays or nucleic acid hybridizations.

Attachment of the capture reagent or enzyme-labeled detector to a solid support, whether direct or indirect, covalent or non-covalent, can be achieved using well-known techniques.

Suitable supports include synthetic polymer supports such as polystyrene, polypropylene, substituted polystyrene, e.g., aminated or carboxylated polystyrene; polyacrylamides; polyamides; polyvinylchloride, etc.; silica, glass beads; magnetic particles; agarose; nitrocellulose; nylon; polyvinylidenedifluoride; surface-modified nylon, etc.

The enzyme-labeled detector can be any reagent useful in assays whether immunoassays or nucleic acid hybridizations. Examples of such detectors include enzyme-labeled members of specific binding pairs whether immune or non-immune. Immune specific binding pairs are exemplified by antigen-antibody systems or hapten-anti-hapten systems. Non-immune binding pairs include systems wherein the two components share a natural affinity for each other but are not antibodies. Exemplary non-immune pairs are biotin-streptavidin intrinsic factor-Vitamin $B_{12}$, folic acid-folate binding protein, thyroxine—thyroxine binding globulin, estrogen—estrogen receptor, and the like.

Any enzyme which can be used as a label or reporter can be used. Conjugation of the enzyme to any of the above-mentioned reagents to form a detector reagent can be effected using conventional techniques.

The following examples illustrate the practice of the invention but should not be construed as a limitation thereon.

EXAMPLE 1

The stability of DEA was evaluated using an alkaline phosphatase (AP) assay with colorimetric detection.

DEA 2.4M (Vista DEA lot 8FDB87, E. I. du Pont de Nemours and Company, Wilmington, Del.) was stored at 4° and 37° without any stabilizing agent and at 37° with 0.108M hydroxylamine hydrochloride as the stabilizing agent. At the time of assay, 5 mL of the DEA was removed to which 75 μL of 200 mM p-nitrophenyl phosphate (PNPP) was added. .2.5 ng of AP in 30 μL of TRIS was added to 160 μL of the PNPP in DEA and the enzyme activity was monitored by the rate of p-nitrophenylate ion (PNP) formation at 405 nm on a COBAS BIO (Roche Analytical Instruments, Nutley, N.J.). The alkanol amine buffer was stabilized using hydroxylamine hydrochloride such that enzyme activity was colorimetrically determined without encountering substantial interference from any degradation of the alkanol amine buffer. In addition, the results presented in Table 1 show that the colorimetric detection of enzyme activity was not adversely affected by the presence of hydroxylamine hydrochloride stabilizing agent.

TABLE 1

Stability of DEA in Colorimetric AP Assay
Alkaline Phosphatase Activity measured at
405 nm (mA/min)

| Day | 4° | 37° | 37° + hydroxylamine |
|---|---|---|---|
| 0 | 611 | 601 | 593 |
| 1 | 618 | 613 | 596 |
| 4 | 635 | 634 | 619 |
| 7 | 648 | 636 | 627 |
| 18 | 669 | 658 | 641 |

EXAMPLE 2

Various reagents were added to solutions of DEA 2.4M as set forth in Tables 2A and 2B. The concentration of the reagent added is as indicated in Tables 2A and 2B. The solutions were maintained at 37° C. except for sample "f" which was maintained at 4° C. Different aliquots were withdrawn at various times to optically determine whether or not background was substantially maintained with respect to each reagent used in this evaluation. Such determination was made in two ways:
1) using a fluorescence background measurement and
1) using an alkaline phosphatase assay method as described below.

A mixture of 375 μL of the DEA solution mentioned above, 20 μL of a 5% bovine serum albumin free of alkaline phosphatase (for background measurement) or 10 ng/mL AP (for enzyme activity measurement) and 75 μL of 15 mM 4-methylumbelliferyl phosphate in 0.5M sodium hydroxide were mixed and incubated at 37° C. for 5 min. Five hundred microliters of a quench buffer, 0.5M EDTA, pH 9.0, di-sodium salt was added to the mixture to stop the enzyme reaction. Eight hundred microliters of which was mixed with 1.5 mL of quench buffer in a cuvette and the fluorescence was measured with a Aminco Fluorometer (SLM AMINCO SPF-500C, SLM Instrument Inc., Urbana, Ill.) at 475 nm Emission, 10 nm bandpass and 375 nm Excitation, 4 nm bandpass.

The results are summarized in Tables 2A and 2B. Hydroxylamine hydrochloride and sodium sulfite both significantly stabilized DEA without inhibiting enzyme activity and did not interfere substantially with the fluorimetric determination in the wavelength region of measurement.

TABLE 2A

Evaluation of Various Reagents as Stabilizing Agents Using
Fluorescent Background Measurement

| Reagent | Day 0 | Day 3 | Day 6 | Day 8 |
|---|---|---|---|---|
| | (Fluorescent Unit) | | | |
| a) 0.16 M sodium sulfite | 0.43 | 0.40 | 0.43 | 0.42 |
| b) 0.019 M sodium hypophosphite | 0.38 | 0.44 | 0.59 | 0.73 |
| c) 0.144 M hydroxylamine hydrochloride | 0.42 | 0.45 | 0.41 | 0.41 |
| d) 0.063 M sodium thiosulfate | 0.39 | 0.42 | 0.46 | 0.48 |
| e) no additive | 0.44 | 0.44 | 0.58 | 0.71 |
| f) no additive at 4° C. | 0.39 | 0.37 | 0.36 | 0.35 |

TABLE 2B

Evaluation of Various Reagents As Stabilization Agents
Using Alkaline Phosphatase Activity Measurement

| Reagent | Day 0 | Day 3 | Day 6 | Day 8 |
|---|---|---|---|---|
| | (Fluorescent Unit) | | | |
| a) 0.016 M sodium sulfite | 14.14 | 13.70 | 13.55 | 13.51 |
| b) 0.019 M sodium hypophosphite | 14.68 | 13.59 | 12.91 | 12.77 |
| c) 0.144 M hydroxylamine hydrochloride | 14.12 | 14.14 | 13.58 | 13.74 |
| d) 0.063 M sodium thiosulfate | 14.43 | 13.31 | 13.14 | 12.83 |
| e) no additive | 14.44 | 13.68 | 12.92 | 12.87 |
| f) no additive at 4° C. | 14.43 | 14.51 | 13.41 | 13.85 |

EXAMPLE 3

Various hydroxylamine derivatives were added in the amounts indicated in Table 3 below to solutions of DEA 2.4M. The solutions were stored at 37° C. At different times aliquots were withdrawn for evaluation of background interference by reading the absorbance of the solution at 365 nm with an HP 8450 Diode Array Spectrophotometer (Hewlett Packard, Palo Alto, Calif.). The results are summarized in Table 3 below. It was found that hydroxylamine salts and O-alkyl hydroxylamine salts were effective in stabilizing DEA over approximately two weeks at 37° C.

TABLE 3

Evaluation of
Stabilization of DEA by Hydroxylamine Derivatives
Absorbance at 365 nm Measurement

| Reagent | Concentration | Day 0 | Day 3 | Day 7 | Day 16 |
|---|---|---|---|---|---|
| A | 0.029 M | 0.006 | 0.026 | 0.037 | 0.266 |
| A | 0.144 M | 0.010 | 0.028 | 0.037 | 0.056 |
| B | 0.012 M | 0.010 | 0.030 | 0.064 | — |
| B | 0.061 M | 0.006 | 0.024 | 0.036 | 0.061 |
| C | 0.024 M | 0.020 | 1.383 | * | * |
| C | 0.120 M | 0.030 | 0.747 | 1.63 | * |
| D | 0.021 M | 0.008 | 0.161 | 0.499 | 2.50 |
| D | 0.103 M | 0.025 | 0.162 | 0.428 | 1.544 |
| E | 0.024 M | 0.003 | 0.016 | 0.018 | 0.026 |
| E | 0.118 M | 0.006 | 0.013 | 0.016 | 0.016 |
| F | | 0.004 | 0.105 | 0.277 | 0.703 |

A = Hydroxylamine hydrochloride
B = Hydroxylamine sulfate
C = N-methyl hydroxylamine hydrochloride
D = N,N-dimethyl hydroxylamine
E = Methoxylamine hydrochloride
F = No additive
— = Sample contaminated
* = Absorbance too high to read

EXAMPLE 4

A carcinoembrionic antigen (CEA) immunoassay was used to demonstrate the effectiveness of stabilization of DEA using the method of the present invention, relative to unstabilized DEA. The immunoassay relied on the presence of CEA antigen to form a capture antibody—CEA—enzyme labeled—detector reagent complex on a chromium dioxide solid phase.

The anti-CEA antibody (capture reagent) was coated on chromium dioxide particles as described in the Birkmeyer et al., Clinical Chemistry, 33(9):1543-1547 (1987), the disclosure of which is hereby incorporated by reference.

50 microliters of CEA-containing serum and 25 μl of chromium dioxide particles coated with anti-CEA antibody as the capture reagent were added to 50 μl of an enzyme-labeled detector reagent. The enzyme-labeled detector reagent was prepared as follows:

20 mg of anti-CEA-F (ab')$_2$ (Hybritech Inc., LaJolla, Calif.) in phosphate buffered saline (PBS) (5 mg/mL) was reacted with a 15 molar excess of N-succinimidyl-4-(N-maleimido-methyl) cyclohexane-1-carboxylate (SMCC) (Pierce Chemical Co., Rockford, Ill.) for ½ hour at room temperature to produce an anti-CEA-F (ab')$_2$ fragment having a thiol reactive group. This activated antibody fragment was purified by Sephadex G-25 chromatography.

30 mg of AP in (PBS) (5 mg/mL) was reacted with an 8.5 molar excess of N-succinimidyl-3-(2-pyridyldithio)propionate (SPDP) for ½ hour at room temperature to produce AP having free thiol groups. Dithiothreitol (DTT) was then added to the reaction mixture to obtain a final concentration on 0.1 mM and allowed to react for an additional ½ hour at room temperature. Activated AP was purified by Sephadex G-25 chromatography.

Both proteins (i.e., the activated antibody fragment and activated enzyme (AP)) were diluted to a final concentration of 1 mg/mL using PBS.

Equal molar concentrations of the activated antibody fragment and activated enzyme were reacted for 1 hour at room temperature and the reaction was quenched by adding N-ethyl maleimide to a final concentration of 1 mM.

The reaction mixture was concentrated and purified by HPLC/GF-450 chromatography. The resulting conjugate was pooled and diluted with 10 mM TRIS, 172 mM NaCl pH 8.5 (TBS).

The mixture containing the CEA containing serum, capture reagent, and detector reagent was incubated at 37° C. for 36 minutes to produce a capture antibody-CEA-enzyme-labelled-detector-reagent complex. The chromium dioxide particles were washed with a wash buffer, 0.25M Tris buffer (pH 7.85) containing 0.05% Tween 20. To a series of separate preparations of this mixture was added 375 μl of DEA buffer and 75 μl of 4-methylumbelliferyl phosphate (0.015M in 0.5M sodium hydroxide) and incubated at 37° C. for 5 minutes. Stabilization and reduction of background fluorescence of hydroxy coumarin ester enzyme substrates is described in Applicants Assignee's copending patent application U.S. Ser. No. 07/242,598 filed Sep. 12, 1988 (Attorney Docket No. IP-0716). The storage history of the DEA buffer for each preparation differed, as described below. The fluorescence of each solution was measured with an excitation wavelength of 365 nm and emission wavelength of 450 nm.

The DEA buffers were prepared as follows: High density polyethylene bottles were filled to 50% capacity with DEA buffer (2.4M, pH 8.9) either without, or with the addition of, hydroxylamine hydrochloride (0.108M) as stabilizer. Simulated use of these materials after storage was achieved by storing, in the uncapped bottles, at 37° C. for 48 and 120 hours. The buffer solutions were all prepared at the same time. Those designated for the "120 hour" study were placed in an incubator at 37° C., while the remainder were stored at 4° C. 72 hours later the "48 hour" buffer samples were placed in the incubator. Thus, after a 120 hour time interval, the buffers had been maintained at 37° C. for the requisite time. All samples had been exposed to the 37° C. environment for either 0, 48 or 120 hours and could be evaluated simultaneously. The results are shown in Table 4.

TABLE 4

| | Stabilization of DEA used in CEA Immunoassay | | | |
|---|---|---|---|---|
| Time (hours) | DEA with Hydroxylamine | % Change | DEA without Hydroxylamine | % Change |
| 0 | 942 | — | 1019 | — |
| 48 | 966 | 2.5 | 963 | 5.4 |
| 120 | 959 | 1.8 | 867 | −15 |

What is claimed is:

1. A method for stabilizing an alkanol amine buffer used in fluorescent determinations of enzymatic activity in an immunoassay which comprises adding a stabilizing effective amount of a stabilizing agent to the buffer wherein the stabilizing agent (i) is selected from the group consisting of hydroxylamine, alkoxylamine or salts thereof, (ii) does not inhibit enzyme activity and (iii) minimizes the formation of degradation products which interfere with fluorescence detection.

2. A method according to claim 1 wherein the alkanol amine buffer is selected from the group consisting of monoethanolamine, diethanolamine, triethanolamine, 2-amino-2-methyl-1-propanol, and tris(hydroxymethyl)aminomethane.

3. A method according to claim 1 wherein the buffer is diethanolamine and the stabilizing agent is hydroxylamine hydrochloride.

4. An immunoassay for detecting and/or quantitating the presence or absence of an analyte in a sample which comprises:

a) contacting, simultaneously or sequentially, the sample suspected to contain the analyte with a capture reagent and an enzyme-labeled detector; and b) detecting or quantitating, by fluorescence, the product of step (a) in the presence of an alkanol amine buffer;

wherein the buffer has been stabilized by adding a stabilizing effective amount of a stabilizing agent to the buffer wherein the stabilizing agent (i) is selected from the group consisting of hydroxylamine, alkanollamine or salts thereof, (ii) does not inhibit enzyme activity and (iii) minimizes the formation of degradation products which interfere with fluorescence detection.

5. A method according to claim 4 wherein the alkanol amine buffer is selected from the group consisting of monoethanolamine, diethanolamine, triethanolamine, 2-amino-2-methyl-1-propanol, and tris(hydroxymethyl)aminomethane.

6. A method according to claim 4 wherein the buffer is diethanolamine and the stabilizing agent is hydroxylamine hydrochloride.

* * * * *